United States Patent [19]

Tada et al.

[11] Patent Number: 5,017,674

[45] Date of Patent: May 21, 1991

[54] EPOXY RESIN COMPOSITION FOR COMPOSITE MATERIAL FROM M- OR O-SUBSTITUTED TRIGLYCIDYLAMINOPHENOLS, WITH FORTIFIER AND LATENT CURING AGENTS

[76] Inventors: Hisashi Tada, 2-1-1 Nekogahori-dohri, Chigusa-ku, Owariasahi; Yoshinobu Shiraishi, 6-6 Midorigaoka, Midori-cho, Owariasahi; Shigetsuga Hayashi, 4-4-1 Shinpo-cho, Chigusa-Ku, Nagoya, all of Japan

[21] Appl. No.: 544,649

[22] Filed: Jun. 27, 1990

Related U.S. Application Data

[62] Division of Ser. No. 303,274, Jan. 30, 1989, Pat. No. 4,956,411.

[30] Foreign Application Priority Data

Feb. 5, 1988 [JP] Japan .................................. 63-25204
Feb. 5, 1988 [JP] Japan .................................. 63-25205
Feb. 5, 1988 [JP] Japan .................................. 63-25206

[51] Int. Cl.$^5$ ..................... C08G 59/46; C08G 59/56; C08G 59/60
[52] U.S. Cl. ......................................... 528/93; 528/99; 528/120; 428/413; 525/482; 525/483; 525/484
[58] Field of Search ..................................... 528/93, 99

[56] References Cited

U.S. PATENT DOCUMENTS

| | | | |
|---|---|---|---|
| 2,951,822 | 9/1960 | Reinking | 528/104 |
| 2,951,825 | 9/1960 | Reinking | 528/99 |
| 4,480,082 | 10/1984 | McClean et al. | 528/103 |
| 4,714,648 | 12/1987 | Nagata | 528/120 |
| 4,767,805 | 8/1988 | Tada et al. | 523/468 |
| 4,900,848 | 2/1990 | Saito et al. | 528/99 |
| 4,956,411 | 9/1990 | Tada et al. | 528/93 |

FOREIGN PATENT DOCUMENTS 0217657 8/1987 European Pat. Off. .

*Primary Examiner*—Earl Nielsen
*Assistant Examiner*—Frederick Krass

[57] ABSTRACT

An epoxy resin composition is disclosed that can be cured at a temperature of 150° C. or below, and can be used to provide a high performance carbon fiber composite material having a 0° direction bending strength of 220 kg/mm$^2$ or over, and an interlayer shear strength of 10 kg/mm$^2$ or over.

The composition is made up of:

(A) an epoxy compound containing 10 to 100% by weight of m- or o-methyl-p-N,N-diglycidylaminophenyl-ether or its oligomer, (B) diaminodiphenylsulfone and/or diaminodiphenylmethane, (C) dicyandiamide, 2,6-xylenylbiguanide, o-tolylbiguanide, diphenylguanidine, adipil dihydrazide, azelayl dihydrazide, or isophthalic acid dihydrazide, and (D) a urea compound.

7 Claims, No Drawings

EPOXY RESIN COMPOSITION FOR COMPOSITE MATERIAL FROM M- OR O-SUBSTITUTED TRIGLYCIDYLAMINOPHENOLS, WITH FORTIFIER AND LATENT CURING AGENTS

This is a division of application Ser. No. 07/303,274, filed on Jan. 30, 1989 now U.S. Pat. No. 4,956,411.

The present invention relates to an epoxy resin composition for composite materials that is composed of a specific polyglycidyl derivative and a curing agent for epoxides.

Since fiber reinforced composite materials containing carbon fibers, alumina fibers or all aromatic polyamide fibers as a reinforcing material have excellent mechanical performance, they are used for structural parts in various industries and also for sporting and leisure goods, or the like. Although various materials have been used as a matrix resin for carbon fiber composite materials, epoxy resins have been widely used because, for example, they are excellent in mechanical properties, have no volatile component at the time of the curing, shrink less at the time of the curing, and are excellent in adhesion to carbon fibers (Japanese Patent Publication No. 40975/1983, and Japanese Patent Application Laid-Open No. 57416/1987). The 0° direction bending strength (converted as the value of that having a fiber volume content of 60%) of the composite materials in which reinforcing fibers are laminated in one-direction has been on the order of 190 kg/mm$^2$ and the interlayer shear strength has been on the order of 10 kg/mm$^2$. Against these present conditions, various studies to improve the mechanical or physical properties and to improve the heat resistance have been made. In Japanese Patent Publication No. 15570/1987, as a composition that can provide a composite material high in interlayer shear strength, an epoxy resin composition comprising diaminodiphenylsulfone and an epoxy resin consisting of N,N-diglycidyl-aminophenylglycidyl-ether and/or N,N-diglycidylaniline is disclosed. When this composition was used, a composite material having an interlayer shear strength of 12.8 kg/mm$^2$ could be obtained, but the 0° direction bending strength was at most 192 kg/mm$^2$. Further, since the curing temperature at which the composite material is molded is as high as 170° C., and it is required to carry out an after-treatment at a temperature that is as high as 190° C., the epoxy resin composition lacked general-purpose properties. Japanese Patent Application Laid-Open Nos. 183340/1987, 183341/1987, and 183342/1987 disclose, as resin compositions that can improve physical properties and heat resistance, three compositions, i.e., a composition (I) consisting of a polyglycidyl derivative of 4-amino-m-cresol and/or 4-amino-o-cresol and diaminodiphenylsulfone and/or diaminodiphenylmethane, a composition (II) consisting of N,N,N',N'-tetraglycidyl-(amino-phenyl)methane and/or its condensate, a polyglycidyl derivative of 4-amino-m-cresol and/or 4-amino-o-cresol and/or its condensate, and diaminodiphenylsulfone and/or diaminodiphenylmethane, and a composition (III) consisting of a phenol-novolak type epoxy resin, a cresol-novolak type epoxy resin and/or a bisphenol A diglycidyl ether type epoxy resin, a polyglycidyl derivative of 4-amino-m-cresol and/or 4-amino-o-cresol and/or its condensate, and dicyandiamide or an acid hydrazide type compound. Although a 0° direction bending strength of 215 kg/mm$^2$ and an interlayer shear strength of 13.6 kg/mm$^2$ can be accomplished by the compositions (I) and (II), the curing requires 1 hour at 150° C., and the postcuring requires 4 hours at 180° C., which is a long period at a high temperature. In the case of the composition (III) whose curing requires 1 hour at 120° C. and whose postcuring requires 2 hours at 130° C., the 0° direction bending strength is 210 kg/mm$^2$, and the interlayer shear strength is 11.2 kg/mm$^2$, the values being rather small.

As stated above, in the case of the use of a polyglycidyl derivative of 4-amino-m-cresol and/or a polyglycidyl derivative of 4-amino-o-cresol as an epoxy compound, if diaminodiphenylsulfone is used as a curing agent, it is required in order to obtain enough physical properties of the composite material that the curing is effected at 150° C. or over and the postcuring is effected at a high temperature of 180° C., which means the composition lacks general-purpose properties. If dicyandiamide is used as a curing agent, the curing can be effected at a low temperature of 120° to 130° C., but the bending strength and the interlayer shear strength of the composite material using the thus obtained resin composition become low.

Taking the above present state into consideration, various studies have been made, and it has been found that an epoxy resin composition for composite materials which can be cured at a temperature of 150° C. or lower and whose 0° direction bending strength and interlayer shear strength are higher in comparison with the prior art can be obtained by combining a specific epoxy compound (A), a curing agent (B) such as diaminodiphenyl compound, another curing agent (C) such as dicyandiamide, a curing accelerator (D) such as an urea compound, and if desired, a reaction product obtained by reacting at least one of amide or amine compounds represented by the following general formula (1), (2) or (3) and at least one of epoxy compounds represented by the following general formula (4) or (5), and a reinforcing material such as a carbon fiber.

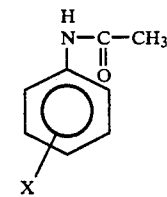

(1)

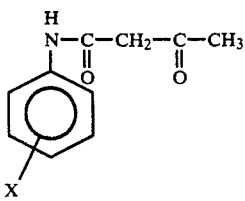

(2)

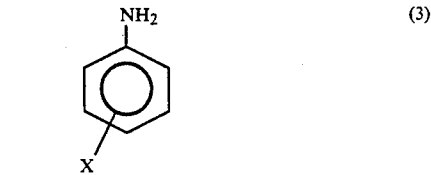

(3)

-continued

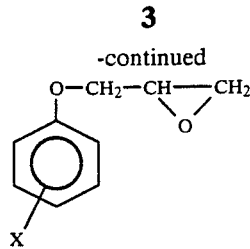   (4)

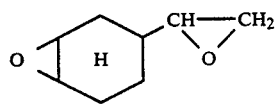   (5)

The present invention is directed to an epoxy resin composition for composite materials comprising, as essential components:

(A) an epoxy compound containing 10 to 100% by weight of m- or o-methyl-p-N,N-diglycidyl-aminophenylglycidyl-ether or its oligomer, (B) a diaminodiphenylsulfone and/or a diaminodiphenylmethane in an amount of 50 to 200% for the total epoxy equivalent of the epoxy compound, (C) 1 to 10 parts by weight of at least one compound selected from the group consisting of dicyandiamide, 2,6-xylenylbiguanide, 0-tolylbiguanide, diphenylguanidine, adipyl dihydrazide, azelayl dihydrazide, and isophthalic acid dihydrazide for 100 parts by weight of the epoxy compound, (D) 1.5 to 15 parts by weight of one or more of urea compounds represented by the following general formula:

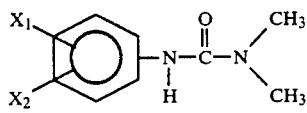

wherein $X_1$ and $X_2$, which may be the same or different, each represents —Cl, —Br, —NO$_2$, —CH$_3$, —H, —OCH$_3$, —C$_2$H$_5$, or

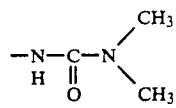

for 100 parts by weight of the epoxy compound.

If necessary, to the epoxy resin composition is added a reaction product (hereinafter referred to as reaction product E) that is obtained by reacting at least one of amide or amine compounds represented by the general formula (1), (2) or (3) given below with at least one of epoxy compounds represented by the general formula (4) or (5) given below in an amount of 5 to 100% by weight based on the amount of the epoxy resin compound comprising the components (A) to (D).

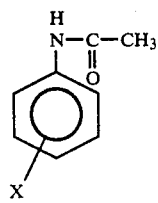   (1)

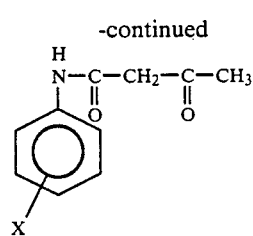   (2)

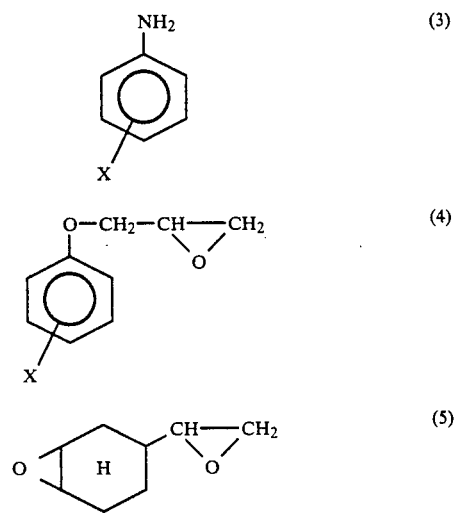

wherein X represents —H, —Cl, —Br, or —OH.

According to the present invention, by using a specific epoxy compound, a curing agent, and a curing accelerator in combination, an epoxy resin composition can be for the first time provided which can cure at 150° or below in a short period of 1 hour, and exhibits such high performance when used together with carbon fibers as a reinforcing material that the 0° direction bending strength is 220 kg/mm$^2$ or over, and the interlayer shear strength is 10 kg/mm$^2$ or over, and whose uncured resin viscosity changes less at room temperature and whose pot life is long. The reason why the reaction product (E) is added if desired in the present invention is that the water resistance of the composite material can be improved without lowering the bending strength and the interlayer shear strength in comparison with the case of the resin composition free from such a reaction product (E), and therefore lowering of the physical properties of the composite material due to the absorption of water becomes less thereby particularly allowing the composite material to be used in a field where water resistance is required.

The epoxy compound used as component (A) in the present invention can be easily produced by reacting m- or o-methyl-p-aminophenol with an excess amount of epichlorohydrin in the presence of lithium hydroxide to have the epoxy group ring-opening addition, then removing the unreacted epichlorohydrin, and dehydrochlorinating with sodium hydroxide (Japanese Patent Publication No. 17970/1962).

The content of m- or o-methyl-p-N,N-diglicidyl-aminophenyl-ether or its origomer in the component (A) is in the range of 10 to 100% by weight of the total of the epoxy compounds. If the content of the epoxy compound is less than 10%, it is not preferable because the bending strength and the interlayer shear strength of the fiber composite material become lower, and the curing properties at low temperatures becomes poor.

Epoxy compounds that can be used together with the component (A) are ones that can be cured with the components (B) and (C) that are curing agents, and examples thereof are polyfunctional epoxy resins such as glycidyl ethers of bisphenol compounds such as bisphenol A, bisphenol F, and bisphenol S, glycidyl ethers of phenol- or cresol-novolak resins, tetraglycidylamine of diaminodiphenylmethane, and triglycidyl compounds and/or triglycidyl ethers of m- or o-aminophenol or triphenylolmethane. Of these epoxy resins, trifunctional or more higher polyfunctional epoxy resins, or phenol-novolak type epoxy resins, or cresol-novolak type epoxy resins are preferable with phenol-novolak type epoxy resins and cresol-novolak type epoxy resins particularly preferred. These epoxy resins may be used alone or in combination. Other modifiers may be added such as polyamides, polyvinyl formal, polyether imides, polysulfones, and polyethersulfones. A compound such as amines or acid anhydrides may be reacted in an amount of up to equivalent to the epoxy group contained in the epoxy compound or the mixture containing the epoxy compound so that the viscosity may be adjusted within a range where gelling would not occur.

As a diaminodiphenylsulfone or a diaminodiphenylmethane (component B) used in the present invention can be mentioned 4,4'-diaminodiphenylsulfone, 3,3'-diaminodiphenylsulfone, 4,4'-diaminodiphenylmethane, and 3,3'-diaminodiphenylmethane and mixtures of these. 4,4'-Diaminodiphenylsulfone is used preferably. The amount of the diaminodiphenyl compound used is in the range of 50 to 200%, preferably 50 to 150%, for the total epoxy equivalent in the epoxy compound or the mixture containing the epoxy compound. If the amount is less than 50%, the crosslinking density becomes low, and the physical properties of the composite material using the resin composition unpreferably lowers, while if the amount is over 200%, it is not preferable because the number of the unreacted amino groups increases and the physical properties of the obtained composite material become lower.

In the present invention, a curing agent that is the component (C) and a curing accelerator that is the component (D) are used together with the diaminodiphenyl compound (component B). As the curing agent (component C), dicyandiamide is preferably used, and as the curing accelerator (component D), 3-(3,4-dichlorophenyl)-1,1-dimethylurea is preferably used which is a compound represented by the general formula above wherein $X_1$ and $X_2$ are —Cl.

In the present invention, if desired, a reaction product (E) that is obtained by reacting at least one of amine or amide compounds represented by the general formula (1), (2) or (3) given below with at least one of epoxy compounds represented by the general formula (4) or (5) given below is added.

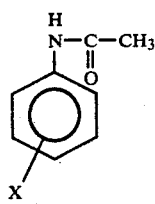
(1)

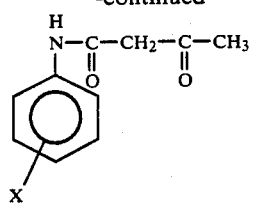
(2)

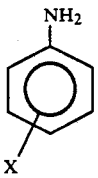
(3)

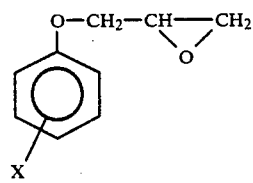
(4)

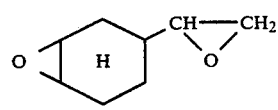
(5)

wherein X represents —H, —Cl, —Br, or —OH.

Although the amides and amines represented by the formula (1), (2) or (3) and the epoxy compounds represented by the formula (4) or (5) may be combined without specific restriction, but preferable examples are the following three: the reaction product [hereinafter referred to as (E)-1] of

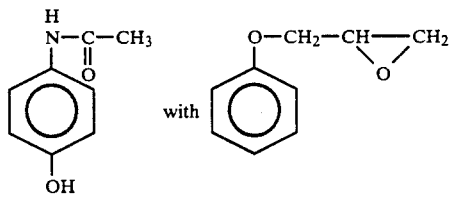

the reaction product [hereinafter referred to as (E)-2] of

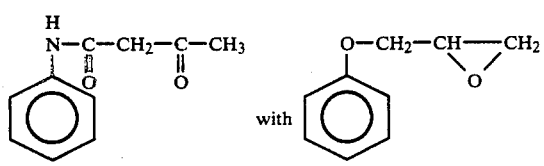

the reaction product [hereinafter referred to as (E)-3] of

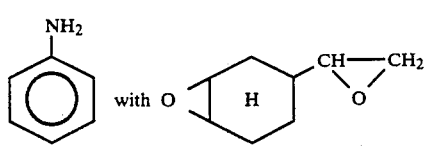

To obtain the reaction product (E) of the amides or amines represented by one of the formulae (1) to (3)

with the epoxy compounds represented by the formula (4) or (5), the compounds are reacted in a molar ratio of from 1:0.9 to 1:1.1 at a temperature ranging from 100° to 200° C. Although the reaction product thus obtained may be used as the reaction product (E) as it is, it is preferable to heat the product at 50° to 200° C. under reduced pressure (1 mm Hg) after the reaction to remove unreacted components. The product thus refined is used as the reaction product (E). The amount of the reaction product (E) to be added is in the range of 5 to 100% by weight of the epoxy resin composition comprising the components (A) to (D). If the amount of the reaction product (E) to be added is less than 5% by weight, the effect for improving the water resistance is less and the water resistance is similar to that of the case where it is not added, while the amount is more than 100% by weight, it is not preferable because the 0° bending strength and the interlayer shear strength become lower.

The resin composition of the present invention is used effectively as an intermediate material for carbon fibers composite materials. The carbon fibers used may be in any of forms for example in the form of a tape, a sheet, a mat, or a fabric wherein carbon fibers are arranged in one direction. Instead of carbon fibers, glass fibers, organic fibers, or metal fibers may be used, which may of course be used together with carbon fibers.

The obtained composite material can be cured at a low temperature of 150° C. or below, and if carbon fibers are used as a reinforcing material, a composite material having such high performance that the 0° direction bending strength is 220 kg/mm² or over and the interlayer shear strength is 10 kg/mm² can be obtained.

The carbon fiber composite material using the present epoxy resin composition as a matrix resin has such physical properties that the 0° direction bending strength is 220 kg/mm² or over and the interlayer shear strength is 10 kg/mm² or over, and can be cured at a low temperature of 150° C. or below. Therefore it is expected that the carbon fiber composite material will be used in various fields such as in the field of sports and leisure wherein it will be used for fishing goods, golf shafts, etc. and in the industrial field wherein it will be used in automobiles, airplanes, rockets, etc.

REFERENCE EXAMPLE 1

Synthesis of m-methyl-p-N,N-diglycidyl aminophenylglycidyl ether [epoxy compound (1)]

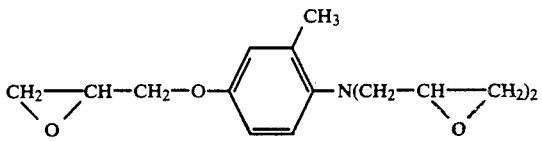

54.6 g (0.444 mol) of m-methyl-p-aminophenol, 370 g (4 mols) of epichlorohydrin, 84 g of 95% ethyl alcohol, 0.65 g of lithium hydroxide monohydrate, and 6 ml (3.7 mol % based on the phenolic hydroxyl group) of water were reacted at room temperature (25° C.) for 137 hours with stirring. The mixture thus obtained was heated to 55° to 60° C., then 66.5 g (1.66 mols) of a 50% by weight of aqueous sodium hydroxide solution were added thereto, and the mixture was heated for 3 hours. The vacuum distillation (under a pressure of 30 mm Hg) was carried out until the temperature of the residual product became 65° C. thereby removing the water, the alcohol and the excess epichlorohydrin. The residual product was dissolved in benzene, and the solution was washed with water repeatedly to remove the salt and the excess sodium hydroxide. The washed benzene solution was subjected to vacuum distillation (under a pressure of 30 mm Hg) thereby removing the benzene. The epoxy equivalent of the resulting dark brown liquid epoxy compound (1) was 105 g/eq.

REFERENCE EXAMPLE 2

Synthesis of o-methyl-p-N,N-diglycidyl aminophenylglycidyl ether [epoxy compound (2)]

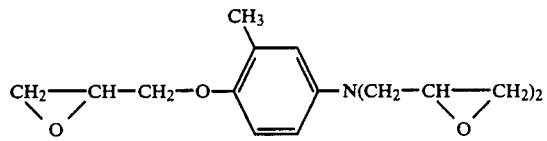

Reference Example 1 was repeated, except that o-methyl-p-aminophenol was used as starting raw material thereby giving an epoxy compound (2). The epoxy equivalent of the resulting epoxy compound (2) was 104 g/eq.

REFERENCE EXAMPLE 3

Synthesis of a reaction product (E)-1 p-Hydroxyacetanilide and phenyl glycidyl ether were mixed in a molar ratio of 1:1.05, and were heated at 160° C. for 60 min, the reaction product being a viscous liquid at room temperature. The reaction product was heated to 150° C. under a pressure of 1 mm Hg to remove the unreacted phenyl glycidyl ether to give a reaction product (E)-1. The infrared absorption spectrum of the reaction product (E)-1 was measured and it was confirmed that it contained no epoxy groups. A chloroform solution of the reaction product (E)-1 was subjected to gel permeation chromatography, and it was found that the reaction product (E)-1 was a reaction mixture containing, in addition to the 1:1 reaction product, a polymeric compound that was resulted from a further reaction.

REFERENCE EXAMPLE 4

Synthesis of a reaction product (E)-2

Reference Example 3 was repeated except that acetacetanilide and phenyl glycidyl ether were used in a molar ratio of 1:1.2, and were heated at 170° C. for 1 hour to give a reaction product (E)-2. The reaction product (E)-2 was found to be a mixture containing, in addition to a 1:1 reaction product, a polymeric compound that was resulted from a further reaction.

REFERENCE EXAMPLE 5

Synthesis of a reaction product (E)-3

Reference Example 3 was repeated except that a mixture of aniline and vinylcyclohexene in a molar ratio of 1:2.1 was heated at 100° C. for 45 min to yield a reaction product (E)-3 in viscous liquid state. The reaction product (E)-3 was found to be a mixture containing, in addition to a 1:1 reaction product, a polymeric compound that was resulted from a further reaction.

EXAMPLES 1 AND 16 AND COMPARATIVE EXAMPLES 1 TO 15

Each of the resin compositions shown in Table 1 was used as a matrix resin and a one-direction carbon fiber composite material was molded, and the bending strength and the interlayer shear strength of each of the molded bodies were measured. The results are shown in Table 1.

The molded bodies shown in Table 1 were made in the following manner. An epoxy resin (A), 4,4'-diaminodiphenylsulfone (B) as a curing agent, dicyandiamide as another curing agent (C), 3(3,4-dichlorophenyl)-1,1-dimethylurea as a curing accelerator (D), and a reaction product (E) were homogeneously mixed in a ratio as shown in Table 1 at a temperature of 60° to 70° C. to form a resin composition for the matrix. The resin composition was heated and was formed into a thin film on a release paper thereby producing a so-called hot melt film. The hot melt film was wound on a drum with the resin composition facing outside (in other words, with the release paper contacting on the surface of the drum), and carbon fibers (Pyrofil ® T-1 manufactured by Mitsubishi Rayon Co., Ltd.) were wound on the resin composition. The fibers and the hot melt film were heated so that the resin composition becomes viscous liquid state and impregnate the fibers and then allowed to cool to form a prepreg. The thus made prepregs were laminated and adjusted so that the content of the carbon fibers after the molding might be 60 vol. %, and then the thus laminated prepregs were loaded in a mold and were heated for a certain period by a hot press heated to a prescribed temperature to form a molded body.

The method of measuring the physical properties of the carbon fiber composite material in the Table 1 was as follows.

(1) The interlayer shear strength

The interlayer shear strength was measured according to ASTM D-2344. A platelike test piece having a length of 15 mm, a width of 10 mm and a thickness of 2 mm was used. The test piece was placed on fulcrum points (whose tips had a radius of 3.2 mm) with the span interval between them being 8 mm, and an indenter having a tip with a radius of 3.2 mm was pressed on the center of the test piece to carry out a three-point test wherein the cross head speed was 2 mm/min. The interlayer shear strength was calculated according to the formula given below. The span interval was designated L (mm), the thickness of the sample was designated T (mm), the width of the sample was designated W (mm), and the breaking load was designated P (kg).

The interlayer shear strength = $3P/4WT$ (kg/mm$^2$)

(2) The bending strength

The bending strength was measured according to ASTM D-790. A platelike test piece having a length of 100 mm, a width of 10 mm and a thickness of 2 mm was used. The test was carried out in the same manner as the interlayer shear strength test, except that the span interval was 80 mm. The 0° direction bending strength was calculated according to the following formula:

Bending strength = $3PL/2WT^2$ (kg/mm$^2$)

In the Table, Ep. 154 denotes a phenol-novolak type epoxy resin (manufactured by Shell Chemical Co., Ltd.), ELM-120 denotes m-N,N-diglycidyl aminophenylglycidyl ether (manufactured by Sumitomo Chemical Co., Ltd.), MY-720 denotes tetraglycidyl diaminodiphenylmethane (manufactured by Chiba-Geigy Co., Ltd.), Ep. 828 denotes bisphenol A type epoxy resin (manufactured by Shell Chemical Co., Ltd.), DADPS denotes 4,4'-diaminodiphenylsulfone, DICY denotes dicyandiamide, and DCMU denotes 3-(3,4-dichlorophenyl)-1,1-dimethylurea. The amount of the reaction product (E) is % by weight of the total amount of the components (A) to (D).

TABLE 1

| Experiment No. | Epoxy compound (1) | Epoxy compound (2) | Ep. 154 | ELM-120 | MY-720 | Ep. 828 | DADPS*1 (phr.) | DICY (phr.) | DCMU (phr.) | Reaction product E*2 (wt. %) | Curing conditions temp. × time [(°C.) × (hr)] | Bending strength (kg/mm$^2$) | Interlayer shear strength (kg/mm$^2$) |
|---|---|---|---|---|---|---|---|---|---|---|---|---|---|
| Example |||||||||||||||
| 1 | 100 | | | | | | 59 | 2 | 4 | — | 140 × 1 | 221 | 12.8 |
| 2 | 100 | | | | | | 59 | 2 | 4 | (E)-1 20 | 130 × 1 | 230 | 13.8 |
| 3 | | 100 | | | | | 59 | 2 | 4 | (E)-1 20 | 130 × 1 | 229 | 14.0 |
| 4 | | 80 | 20 | | | | 52 | 2 | 4 | (E)-1 20 | 130 × 1 | 223 | 13.2 |
| 5 | 50 | | 50 | | | | 44 | 2 | 4 | (E)-1 20 | 130 × 1 | 226 | 14.1 |
| 6 | 20 | | 80 | | | | 38 | 2 | 4 | — | 140 × 1 | 220 | 13.6 |
| 7 | 20 | | 80 | | | | 38 | 2 | 4 | (E)-1 10 | 130 × 1 | 232 | 14.1 |
| 8 | 60 | | | 40 | | | 56 | 2 | 4 | (E)-1 20 | 130 × 1 | 224 | 12.6 |
| 9 | 60 | | | | 40 | | 56 | 2 | 4 | (E)-1 20 | 130 × 1 | 231 | 12.8 |
| 10 | 60 | | | | | 40 | 45 | 2 | 4 | (E)-1 20 | 130 × 1 | 221 | 11.5 |
| 11 | 100 | | | | | | 59 | 2 | 4 | (E)-2 15 | 130 × 1 | 229 | 13.6 |
| 12 | | 100 | | | | | 59 | 2 | 4 | (E)-2 15 | 130 × 1 | 228 | 13.7 |
| 13 | 20 | | 80 | | | | 38 | 2 | 4 | (E)-2 15 | 130 × 1 | 232 | 13.9 |
| 14 | 100 | | | | | | 59 | 2 | 4 | (E)-3 25 | 130 × 1 | 234 | 13.9 |
| 15 | | 100 | | | | | 59 | 2 | 4 | (E)-3 25 | 130 × 1 | 229 | 13.0 |
| 16 | 20 | | 80 | | | | 38 | 2 | 4 | (E)-3 25 | 130 × 1 | 226 | 13.7 |
| Comparative Example |||||||||||||||
| 1 | 5 | | 95 | | | | 36 | 2 | 4 | (E)-1 20 | 150 × 1 | 201 | 9.5 |
| 2 | | 5 | 95 | | | | 36 | 2 | 4 | (E)-1 20 | 150 × 1 | 198 | 9.8 |
| 3 | | | 100 | | | | 35 | 2 | 4 | — | 150 × 1 | curing was insufficient | |
| 4 | | | 100 | | | | 35 | 2 | 4 | (E)-1 20 | 150 × 1 | 181 | 9.1 |

TABLE 1-continued

| Experiment No. | Epoxy compound (wt. %) | | | | | | DADPS*1 (phr.) | DICY (phr.) | DCMU (phr.) | Reaction product E*2 (wt. %) | Curing conditions temp. × time [(°C.) × (hr)] | Bending strength (kg/mm²) | Interlayer shear strength (kg/mm²) |
|---|---|---|---|---|---|---|---|---|---|---|---|---|---|
| | Epoxy compound (1) | Epoxy compound (2) | Ep. 154 | ELM-120 | MY-720 | Ep. 828 | | | | | | | |
| 5 | | | | 100 | | | 52 | 2 | 4 | — | 150 × 1 | curing was insufficient | |
| 6 | | | | 100 | | | 52 | 2 | 4 | (E)-1 20 | 150 × 1 | 178 | 8.8 |
| 7 | | | | | 100 | | 53 | 2 | 4 | (E)-1 20 | 150 × 1 | curing was insufficient | |
| 8 | | | | | | 100 | 33 | 2 | 4 | (E)-1 20 | 130 × 1 | 189 | 9.6 |
| 9 | 15 | | 50 | | | 35 | 36 | — | — | — | 150 × 1 | curing was insufficient | |
| 10*3 | 15 | | 50 | | | 35 | — | 6 | 4.5 | — | 130 × 1 | 194 | 10.5 |
| 11 | 15 | | 50 | | | 35 | — | 6 | 4.5 | (E)-2 15 | 130 × 1 | 199 | 10.4 |
| 12 | 100 | | | | | | 59 | — | — | (E)-2 15 | 150 × 1 | curing was insufficient | |
| 13 | 100 | | | | | | — | 2 | 4 | (E)-2 15 | 130 × 1 | 181 | 9.8 |
| 14 | 50 | | 50 | | | | 44 | — | — | (E)-2 15 | 150 × 1 | curing was insufficient | |
| 15 | 50 | | 50 | | | | — | 2 | 4 | (E)-2 15 | 130 × 1 | 186 | 10.2 |

*1 An equivalent amount of 4,4'-diaminodiphenylsulfone calculated on the base of the composition of the epoxy compounds was used.
*2 The amount is based on the mixture of the epoxy compounds, DADPS, DICY, and DCMU.
*3 The same resin composition as indicated in the Example disclosed in Japanese Patent Application Laid-Open No. 183342/1987 was used.

As apparent from Table 1, it can be understood that when the resin compositions of the present invention were used as matrix resin, carbon fiber composite materials having a 0° direction bending strength of 220 kg/mm² or over and an interlayer shear strength of 10 kg/mm² could easily be prepared. In contrast, in Comparative Examples, the physical properties of the products cured at a temperature of 150° C. or below lowered, or the curing was insufficient, which made it impossible to measure the physical properties. Particularly, as indicated in Comparative Examples 9 to 15, when diaminodiphenylsulfone or dicyandiamide was used alone, the curing was insufficient, and if it was cured, the bending strength and the interlayer shear strength of the carbon fiber composite material were low. Therefore, it can be understood that when diaminodiphenylsulfone and dicyandiamide were used in combination, the curing could be made at a low temperature in a short period of time, and the 0° direction bending strength and the interlayer shear strength of the carbon fiber composite material increased.

EXAMPLES 17 TO 27 AND COMPARATIVE EXAMPLES 16 AND 17

Examples 1 to 16 were repeated, except that a mixture of the epoxy compound (1)/Ep. 154 (40/60 wt. %) was used and that, the amounts of diaminodiphenylsulfone and the reaction product (E)-1 were varied to prepare epoxy resin compositions, with the heating at 130° C. for 1 hour, thereby producing carbon fiber composite materials. The results of the measurement of the bending strength and the interlayer shear strength of the molded items are shown in Tables 2 and 3.

TABLE 2

| Experiment No. | DADPS (phr) | DADPS (equivalent ratio)*1 | DICY (phr) | DCMU (phr) | Added amount of reaction product (E)-1*2 (wt. %) | Physical properties of carbon fiber composite material | |
|---|---|---|---|---|---|---|---|
| | | | | | | Bending strength (kg/mm²) | Interlayer shear strength (kg/mm²) |
| Comparative Example 16 | 13 | 30 | 2 | 4 | 20 | 209 | 9.8 |
| Example 17 | 21 | 50 | 2 | 4 | 20 | 221 | 11.2 |
| Example 18 | 34 | 80 | 2 | 4 | 20 | 238 | 13.9 |
| Example 19 | 42 | 100 | 2 | 4 | 20 | 237 | 14.0 |
| Example 20 | 55 | 130 | 2 | 4 | 20 | 224 | 12.9 |
| Example 21 | 63 | 150 | 2 | 4 | 20 | 222 | 12.5 |
| Comparative Example 17 | 93 | 220 | 2 | 4 | 20 | 202 | 10.1 |

*1 The amount of added, assuming the equivalent of DADPS, which was calculated theoretically from the epoxy equivalent of the mixture of the epoxy compound (1)/Ep. 154 (40/60), to be 100.
*2 Wt. % based on the mixture of the epoxy compound, DADPS, DICY, and DCMU.

nodiphenylsulfone and dicyandiamide were used in

TABLE 3

| Experiment No. | DADPS*1 (phr) | DICY (phr) | DCMU (phr) | Added amount of reaction product (E)-1*2 (wt. %) | Physical properties of carbon fiber composite material | |
|---|---|---|---|---|---|---|
| | | | | | Bending strength (kg/mm²) | Interlayer shear strength (kg/mm²) |
| Example 22 | 42 | 2 | 4 | 0 | 223 | 12.2 |

TABLE 3-continued

| Experiment No. | DADPS*[1] (phr) | DICY (phr) | DCMU (phr) | Added amount of reaction product (E)-1*[2] (wt. %) | Physical properties of carbon fiber composite material | |
|---|---|---|---|---|---|---|
| | | | | | Bending strength (kg/mm$^2$) | Interlayer shear strength (kg/mm$^2$) |
| Example 23 | 42 | 2 | 4 | 10 | 235 | 13.6 |
| Example 24 | 42 | 2 | 4 | 30 | 232 | 14.1 |
| Example 25 | 42 | 2 | 4 | 50 | 228 | 13.7 |
| Example 26 | 42 | 2 | 4 | 70 | 225 | 13.0 |
| Example 27 | 42 | 2 | 4 | 100 | 221 | 12.8 |

*[1]DBDPS was used in an equivalent amount calculated from the epoxy compound (1)/Ep. 154 = 40/60 (wt. %).
*[2]Wt. % based on the mixture of the epoxy compound, DADPS, DICY, and DCMU.

EXAMPLE 28 AND COMPARATIVE EXAMPLE 18

After the carbon fiber composite material obtained in the same way as in Examples 1 to 16 by using the reaction product (E)-3 was immersed in hot water at 50° C. for 24 hours to allow the composite material to absorb water, the 0° direction bending strength and the interlayer shear strength were measured. The results are shown in Table 4. It is clear that the water absorption of the carbon fiber composite material using the present resin composition was low and therefore the decrease in the physical properties due to the absorption of water was low.

EXAMPLES 29 TO 32

To 100 parts by weight of the epoxy compound (1) prepared in Reference Example 1, 0.1 part by weight of trimethyl amine was added and heated at a temperature of 100° C. for 30 min to obtain a viscous origomer of epoxy compound. Epoxy equivalent of the origomer thus obtained was 196. The origomer was formed through a reaction of a part of epoxy groups in the epoxy compound.

Then, carbon fiber composite materials in which carbon fibers were arranged in one direction were molded using a matrix resin containing the origomer in the same way as in Examples 1 to 16.

TABLE 4

| Example 28; comparative Example 18 Experiment No. | Epoxy compound composition (wt. %) | DADPS*[1] (phr) | DICY (phr) | DCMU (phr) | Added amount of reaction product (E)-3*[2] (wt. %) | Physical properties of carbon fiber composite material | | | | |
|---|---|---|---|---|---|---|---|---|---|---|
| | | | | | | Before absorption of water | | After absorption of water | | |
| | | | | | | Bending strength (kg/mm$^2$) | Interlayer shear strength (kg/mm$^2$) | Water absorption (%) | Bending strength (kg/mm$^2$) | Interlayer shear strength (kg/mm$^2$) |
| 1 | epoxy compound (1) = 100 | 59 | 2 | 4 | 25 | 234 | 13.9 | 0.13 | 229 | 13.1 |
| 2 | epoxy compound (1)/Ep. 154 (80/20) | 52 | 2 | 4 | 25 | 232 | 13.4 | 0.20 | 226 | 13.0 |
| 3 | epoxy compound (1)/Ep. 154 (40/60) | 42 | 2 | 4 | 25 | 231 | 13.7 | 0.41 | 222 | 12.9 |
| 4 | epoxy compound (1)/Ep. 154 (20/80) | 38 | 2 | 4 | 25 | 235 | 14.2 | 0.51 | 226 | 13.5 |
| 1 (comparative) | Ep. 154 = 100 | 35 | 2 | 4 | 25 | 203 | 10.1 | 0.81 | 195 | 9.9 |
| 2 (comparative) | ELM-120 = 100 | 52 | 2 | 4 | 25 | 198 | 10.2 | 0.95 | 189 | 9.7 |
| 3 (comparative) | MY-720 = 100 | 53 | 2 | 4 | 25 | 196 | 9.8 | 1.05 | 181 | 9.0 |
| 4 (comparative) | Ep. 128 = 100 | 33 | 2 | 4 | 25 | 181 | 9.5 | 0.82 | 169 | 8.5 |

*[1]An equivalent amount of DADPS caculated from the epoxy compound composition was used.
*[2]Wt. % based on the mixture of the epoxy compound, DADPS, DICY, and DCMU.

Chemical composition of the matrix resin, and the 0° direction bending strength and the interlayer shear strength of the molded bodies obtained are shown in Table 5.

TABLE 5

| Example | Epoxy compound(1) (Origomer) | DADPS*[1] (phr) | DICY (phr) | DCMU (phr) | Added amount of reaction product E*[2] (wt. %) | Curing conditions: temperature × time [(°C.) × (hr)] | Bending strength (kg/mm$^2$) | Interlayer shear strength (kg/mm$^2$) |
|---|---|---|---|---|---|---|---|---|
| 29 | 100 | 32 | 2 | 4 | — | 140 × 1 | 226 | 12.9 |

TABLE 5-continued

| Example | Epoxy compound(1) (Origomer) | DADPS[*1] (phr) | DICY (phr) | DCMU (phr) | Added amount of reaction product E[*2] (wt. %) | Curing conditions: temperature × time [(°C.) × (hr)] | Bending strength (kg/mm$^2$) | Interlayer shear strength (kg/mm$^2$) |
|---|---|---|---|---|---|---|---|---|
| 30 | 100 | 32 | 2 | 4 | (E)-1 20 | 130 × 1 | 229 | 13.3 |
| 31 | 100 | 32 | 2 | 4 | (E)-2 15 | 130 × 1 | 230 | 13.1 |
| 32 | 100 | 32 | 2 | 4 | (E)-3 25 | 130 × 1 | 232 | 13.5 |

[*1]An equivalent amount of DADPS calculated from the epoxy compound(1) (origomer) was used.
[*2]Wt. % based on the weight of the mixture of the epoxy compound(1) (origomer), DADPS, DICY and DCMU.

EXAMPLES 33 TO 48

Carbon fiber composite materials were prepared in such a method as in Examples 1 to 16 using a matrix resin containing the epoxide compound (1) as epoxy resin, (E)-1 as a reaction product E and such components (B), (C) and (D) in different amounts as shown in Table 6. Chemical composition of the matrix resin and, the 0° direction bending strength and the interlayer shear strength of the molded bodies obtained are shown in Table 6.

TABLE 6

| Experiment No. | Epoxy compound (I) | Component (B) DADPS (phr) | Component (B) DADPM *1 (phr) | Component (C) Compound | Component (C) Added amount (phr) | Component (D) *2 X₁ | Component (D) *2 X₂ | Component (D) Added amount (phr) | Reaction product (E)-1 *3 (wt. %) | Curing conditions: temp. × time [(°C.) × (hr)] | Bending strength (kg/mm²) | Interlayer shear strength (kg/mm²) |
|---|---|---|---|---|---|---|---|---|---|---|---|---|
| 33 | 100 | 59 | — | 2,6-xylenylbiguanide | 2 | —Cl | —Cl | 4 | 20 | 130 × 1 | 231 | 13.1 |
| 34 | 100 | 59 | — | O-tolylbiguanide | 2 | —Cl | —Cl | 4 | 20 | 130 × 1 | 224 | 12.8 |
| 35 | 100 | 59 | — | diphenylbiguanidine | 3 | —Cl | —Cl | 4 | 20 | 130 × 1 | 228 | 12.9 |
| 36 | 100 | 59 | — | " | 5 | —Cl | —Cl | 4 | 20 | 120 × 1 | 231 | 13.0 |
| 37 | 100 | 59 | — | adipyl dihydrazide | 4 | —Cl | —Cl | 4 | 20 | 130 × 1 | 230 | 12.9 |
| 38 | 100 | 59 | — | azelayl dihydrazide | 4 | —Cl | —Cl | 4 | 20 | 130 × 1 | 228 | 13.2 |
| 39 | 100 | 59 | — | isophthalic acid hydrazide | 4 | —Cl | —Cl | 4 | 20 | 130 × 1 | 232 | 13.4 |
| 40 | 100 | — | 59 | DICY | 2 | —Cl | —Cl | 4 | 20 | 120 × 1 | 238 | 13.5 |
| 41 | 100 | 29.5 | 29.5 | " | 2 | —Cl | —Cl | 4 | 20 | 130 × 1 | 232 | 13.5 |
| 42 | 100 | 59 | — | " | 2 | —H | —N(H)—C(=O)—N(CH₃)(CH₃) | 2 | 20 | 120 × 1 | 235 | 13.6 |
| 43 | 100 | 59 | — | " | 2 | —H | —Cl | 4 | 20 | 130 × 1 | 220 | 12.5 |
| 44 | 100 | 59 | — | " | 2 | —Br | —Br | 4 | 20 | 130 × 1 | 228 | 14.1 |
| 45 | 100 | 59 | — | " | 2 | —NO₂ | —NO₂ | 4 | 20 | 130 × 1 | 227 | 13.8 |
| 46 | 100 | 59 | — | " | 3 | —OCH₃ | —OCH₃ | 4 | 20 | 130 × 1 | 222 | 12.4 |
| 47 | 100 | 59 | — | " | 3 | —OC₂H₅ | —OC₂H₅ | 4 | 20 | 130 × 1 | 226 | 12.3 |
| 48 | 100 | 59 | — | " | 2 | —CH₃ | —CH₃ | 5 | 20 | 130 × 1 | 230 | 12.8 |

*1 DADPM denotes diaminodiphenylmethane.
*2 X₁ and X₂ in the Table 6 denote X₁ and X₂ in the formula for the urea compound of component (D).
*3 Wt. % based on the weight of the mixture of the epoxy compound (I), and components (B), (C) and (D).

What is claimed is:

1. An epoxy resin composition for composite materials, comprising:
   (A) an epoxy compound containing 10 to 100% by weight of m- or o-methyl-p-N,N-diglycidyl-aminophenylglycidyl-ether or its oligomer,
   (B) a diaminodiphenylsulfone and/or a diaminodiphenylmethane in an amount of 50 to 200% for the total epoxy equivalent of the epoxy compound,
   (C) 1 to 10 parts by weight of at least one compound selected from the group consisting of dicyandiamide, 2,6-xylenylbiguanide, o-tolylbiguanide, diphenylguanidine, adipyl dihydrazide, azelayl dihydrazide, and isophthalic acid dihydrazide for 100 parts by weight of the epoxy compound,
   (D) 1.5 to 15 parts by weight of one or more of urea compounds represented by the following general formula:

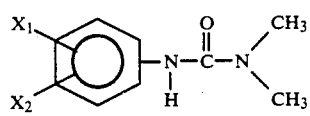

wherein $X_1$ and $X_2$, which may be the same of different, each represents —Cl, —Br, —NO$_2$, —CH$_3$, —H, —OCH$_3$, —C$_2$H$_5$, or

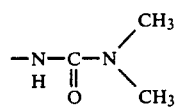

for 100 parts by weight of the epoxy compound, and
   (E) a reaction product obtained by reacting at least one of amide or amine compounds represented by the general formulae (1), (2) or (3) given below with at least one of epoxy compounds represented by the general formulae (4) or (5) given below is additionally contained in an amount of below 100% by weight based on the weight of the epoxy resin composition comprising the components (A) to (D)

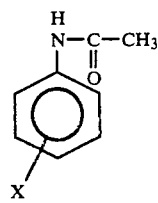  (1)

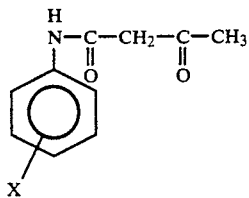  (2)

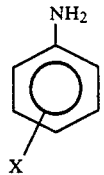  (3)

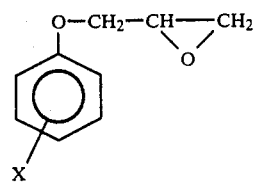  (4)

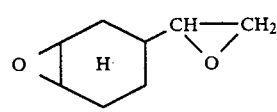  (5)

wherein X represents —H, —Cl, —Br, or —OH.

2. The composition of claim 1, wherein a reaction product of

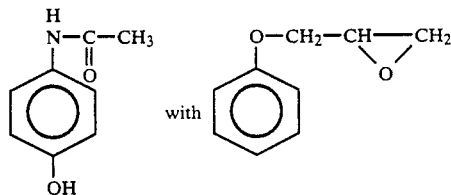

is used.

3. The composition of claim 1, wherein a reaction product of

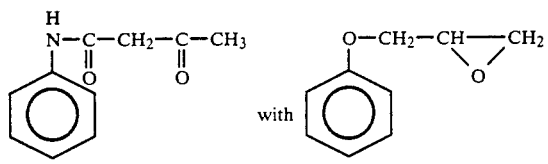

is used.

4. The composition of claim 1, wherein a reaction product of

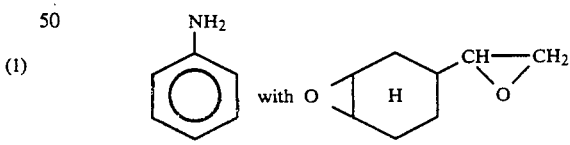

is used.

5. The composition of claim 1, wherein a phenol-novolak epoxy resin and/or a cresol-novolak epoxy resin is used as an epoxy compound in combination with the component (A), that is, m- or o-methyl-p-N,N-diglycidylaminophenylglycidyl-ether or its oligomer.

6. The composition of claim 1, wherein the component (C) is dicyandiamide.

7. The composition of claim 1, wherein each of $X_1$ and $X_2$ in the component (D) represents a chlorine atom.

* * * * *

UNITED STATES PATENT AND TRADEMARK OFFICE
CERTIFICATE OF CORRECTION

PATENT NO. : 5,017,674
DATED : May 21, 1991
INVENTOR(S) : Hisashi Tada et al

It is certified that error appears in the above-identified patent and that said Letters Patent is hereby corrected as shown below:

On the title page, insert --[73] Assignee: Mitsubishi Rayon Company Limited, Tokyo, Japan--.
In tiem [75] Inventors: please correct 1st inventor's address to read --Nagoya--.

Signed and Sealed this

Seventeenth Day of November, 1992

Attest:

DOUGLAS B. COMER

Attesting Officer

Acting Commissioner of Patents and Trademarks